US006617107B1

(12) United States Patent
Dean

(10) Patent No.: US 6,617,107 B1
(45) Date of Patent: Sep. 9, 2003

(54) SPECIFIC OLIGONUCLEOTIDE PRIMERS FOR DETECTION OF BOVINE MALE CHROMOSOME PRESENCE BY POLYMERASE CHAIN REACTION AND METHOD

(75) Inventor: Alan D. Dean, Fort Collins, CO (US)

(73) Assignee: XY, Inc., Fort Collins, CO (US)

( * ) Notice: Subject to any disclaimer, the term of this patent is extended or adjusted under 35 U.S.C. 154(b) by 0 days.

(21) Appl. No.: 09/601,599

(22) PCT Filed: Feb. 3, 1999

(86) PCT No.: PCT/US99/02387

§ 371 (c)(1),
(2), (4) Date: Aug. 3, 2000

(87) PCT Pub. No.: WO99/38883

PCT Pub. Date: Aug. 5, 1999

Related U.S. Application Data

(60) Provisional application No. 60/073,863, filed on Feb. 3, 1998.

(51) Int. Cl.[7] ............... C12B 1/68; C12P 19/34; C07H 21/00; C07H 21/04
(52) U.S. Cl. .............. 435/6; 435/91.2; 435/91.1; 536/22.1; 536/24.3; 536/24.31
(58) Field of Search .............. 435/91.1, 91.2, 435/6; 536/22.1, 24.3, 24.31

(56) References Cited

U.S. PATENT DOCUMENTS

| | | | |
|---|---|---|---|
| 3,644,128 A | * 2/1972 | Lipner ................. 99/108 |
| 4,683,195 A | 7/1987 | Mullis et al. ............ 435/6 |
| 4,683,202 A | 7/1987 | Mullis ................ 435/91 |
| 5,055,393 A | 10/1991 | Kwoh et al. ............ 435/6 |
| 5,437,987 A | 8/1995 | Teng et al. ........... 435/7.25 |
| 5,461,145 A | 10/1995 | Kudo et al. .......... 536/24.41 |
| 5,480,774 A | 1/1996 | Hew et al. ............ 435/6 |
| 5,494,795 A | 2/1996 | Guerry et al. .......... 435/6 |
| 5,578,449 A | 11/1996 | Frasch et al. .......... 435/6 |
| 5,622,820 A | 4/1997 | Rossi ................ 435/5 |
| 5,663,048 A | 9/1997 | Winkfein et al. ........ 435/6 |
| 5,876,942 A | 3/1999 | Cheng et al. ........... 435/6 |
| 5,888,730 A | 3/1999 | Gray et al. ............ 435/6 |

OTHER PUBLICATIONS

The nucleic acid sequence search report, Accesion No. U75895.*

Vogel, Tanja; Deschend, Frank; Manz, Eberhard; Jung, Christian; Jakubiczka, Sybille; Fehr, Susanne; Schmidtke, Jorg; Schnieders, Frank;"Organization and expression of bovine TSPY ", Mammalian Genome 8, 491–496 (1997).

* cited by examiner

Primary Examiner—Ethan Whisenant
Assistant Examiner—Joyce Tung
(74) Attorney, Agent, or Firm—Santangelo Law Offices, P.C.; Craig R. Miles

(57) ABSTRACT

This invention is a specific set of oligonucleotide Polymerase chain reaction (PCR) primers [5'-GTGATCCGGCATATAGCTGAGA-3' (SEQ ID No. 1) and 5'-TGGTCGCTGATCAGGATGGAA-3' (SEQ ID No. 2)] for specific polymerase chain reaction (PCR) amplification of a region of the bovine male-specific chromosome sequence.

16 Claims, 1 Drawing Sheet

1 2 3 4 5 6 7 8 9 10 11 12

1 2 3 4 5 6 7 8 9 10 11 12 ized by the present invention. The disclosure should be understood to encompass and include each such variation be it a variation of any apparatus embodiment, a method embodiment, or even merely a variation of any element of these.

SEQUENCE LISTING

```
<160> NUMBER OF SEQ ID NOS:   2

<210> SEQ ID NO 1
<211> LENGTH: 22
<212> TYPE: DNA
<213> ORGANISM: Artificial Sequence
<220> FEATURE:
<223> OTHER INFORMATION: PCR primer
```

```
<400> SEQUENCE: 1
gtgatccggc atatagctga ga                                              22

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
tggtcgctga tcaggatgga a                                               21
```

SPECIFIC OLIGONUCLEOTIDE PRIMERS FOR DETECTION OF BOVINE MALE CHROMOSOME PRESENCE BY POLYMERASE CHAIN REACTION AND METHOD

This application is the National Stage of International Application No. PCT/US99/02387, filed Feb. 3, 1999 which claims the benefit of U.S. Provisional Application No. 60/073,863, filed Feb. 3, 1998, each hereby incorporated by reference.

I. TECHNICAL FIELD

This invention relates to a specific set of primers for uniquely determining the presence of bovine Y chromosome. Specifically, it includes unique primers for the amplification by a polymerase chain reaction (PCR) methodology of a specific bovine Y chromosome sequence. This invention also relates to a method for detection of the presence of a bovine male chromosome sequence using specific oligonucleotide primers for amplification of the male chromosome sequence by polymerase chain reaction.

II. BACKGROUND

The methodology of polymerase chain reaction (PCR) was invented by Kary Mullis in the mid-1980s and has revolutionized molecular genetics by making possible a whole new approach to the study and analysis of genes. The methodology has become well known since it was invented. PCR allows amplification of a preselected region of DNA and can serve as a highly specific and sensitive detection method (K. B. Mullis and F. A. Faloona, Methods Enzymol. 155:335–350, 1987). Some specific PCR methods have been patented in such patents as U.S. Pat. Nos. 4,683,195 and No. 4,683,202 to Mullis, et al. which are hereby incorporated by reference.

The PCR has also been used for the identification of organisms in complex substrates and to the detection of infectious agents (D. M. Olive, J. Clin. Microbiol. 27: 261–265; B. I. Eisenstein, New Engl. J. Med. 322: 178–183, 1990). Some specific oligonucleotide primers have been developed for detection of pathogenic bacteria by PCR (U.S. Pat. No. 5,494,795). Because of its efficiency and specificity, PCR techniques have been applied extensively to every field in which the molecular techniques are employed and to the detection of presence of a specific gene or a portion of the gene of interest.

Efforts of use of PCR have also been made in the meat and dairy industry. It is practically important to recognize the gender in some applications by detecting the presence of the unique Y chromosome in male cells or tissues. The identification of the presence of any portion of a male chromosome can be important for a number of reasons. One of the reasons is the identification of tissues or meat by gender after the tissues have been removed from the animal and disbursed through marketing channels. By identifying for instance the gender (bull or cow in this case), a determination of proper purchases, representations, and quality of the tissues maybe made. Therefore, efforts of designing appropriate primers have been undertaken and a pair of primers specifically identifying a portion of bovine Y chromsome has been successfully designed by the present inventor. Several aspects of the general bovine sequence had been previously identified prior to the present invention. However, among the aspects unique to this invention are the particular and specific primers complementary to the particular sequence of the bovine male chromosome. Despite attempts by others in the art to test or probe for the Y chromosomes, apparently it escaped those in the field to create such primers uniquely designed to amplify the specific region of the sequence on the Y chromosome to indicate the gender. While other pruners may exist in the marketplace, these primers are unique. By simply using these primers on the tissues, a ready identification of the gender may be made. The prior references do not teach effective or suitable primers to the extent now shown.

III. DISCLOSURE OF THE INVENTION

Accordingly, an object of this invention is a set of oligonucleotide primers [sequence 5'-GTGATCCGGCATATAGCTGAGA-3' (SEQ ID No. 1)] and [sequence 5'-TGGTCGCTGATCAGGATGGAA-3' (SEQ ID No. 2)] for PCR amplification of a portion of bovine Y chromosome DNA sequence.

An additional object of this invention is the demonstration of the specificity of the above oligonucleotide primers for use in detecting the presence of a portion of bovine Y chromosome DNA sequence. This demonstration is specific only to a region of the Y chromosome sequences in bulls but not specific to other chromosome DNA sequences in bulls and chromosome sequences in cows.

These and additional objects of the invention are accomplished by application of standard PCR methodology employing the oligonucleotide primers [5'-GTGATCCGGCATATAGCTGAGA-3' (SEQ ID No. 1) and 5'-TGGTCGCTGATCAGGATGGAA-3' (SEQ ID No. 2)] to amplify a portion of the bovine Y chromosome DNA sequence. The bovine species used in this invention in particular is Bos taurus but these primers might be used in other bovine species and, to-some extent, even in species other than bovines.

IV. BRIEF DESCRIPTION OF THE DRAWINGS

V. SEQUENCE LISTING FREE TEXT

Figure 1:
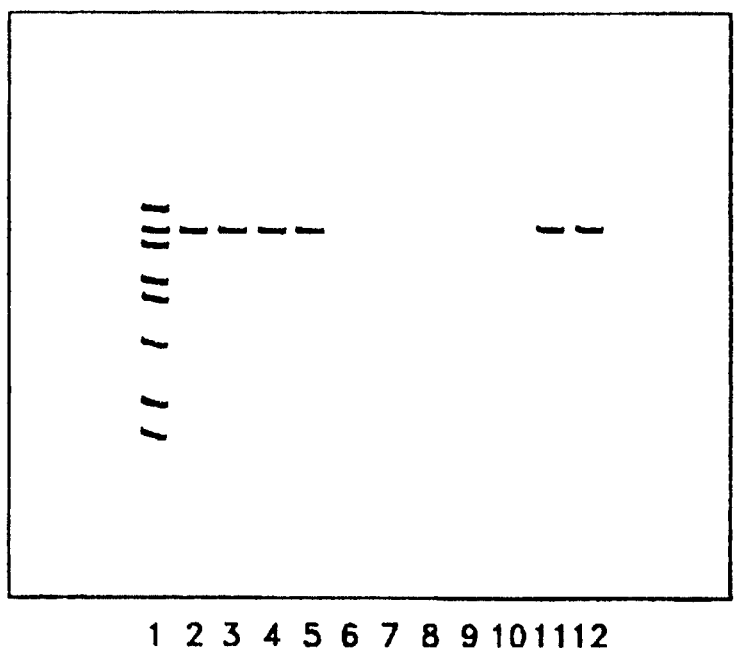
FIG. 1 shows the electrophoretic results of the amplification products obtained using Y-specific primers.
Figure 2:
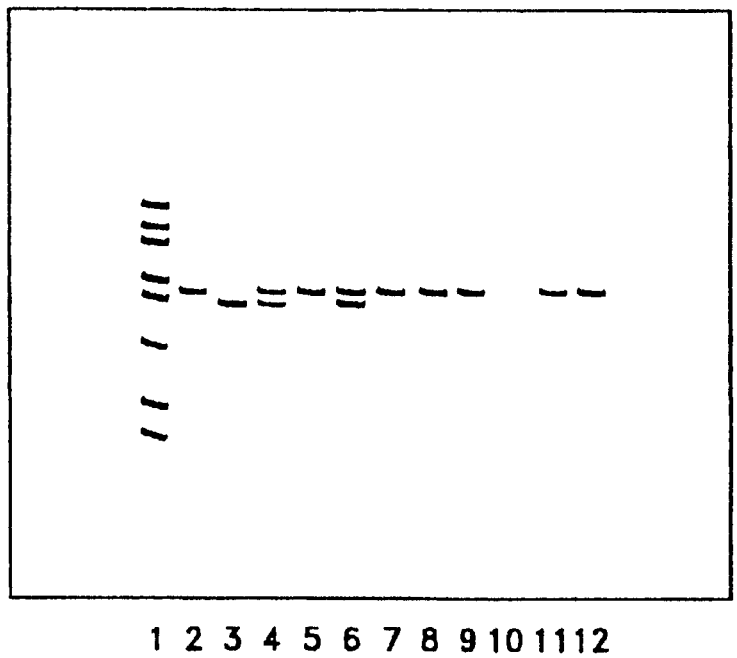
FIG. 2 shows the electrophoretic results of the amplification products obtained using primers specific for the bovine prion gene as a control.

1. The first nucleotide sequence is a forward primer 5'-GTGATCCGGCATATAGCTGAGA-3' (SEQ ID) No. 1).
2. The second nucleotide sequence is a reverse primer 5'-TGGTCGCTGATCAGGATGGAA-3' (SEQ ID No. 2).

VI. BEST MODE FOR CARRYING OUT THE INVENTION

As can be easily understood, the basic concepts of the present invention may be embodied in a variety of ways. It involves techniques as well as devices to accomplish the appropriate invention. In this application, the techniques are disclosed as part of the results shown to be achieved by the various sequences described and as steps which are inherent to utilization. They are simply the natural result of utilizing the sequences as intended and described. In addition, while the sequences are disclosed, it would be understood that these not only accomplish certain methods but also can be varied in a number of ways. Importantly, as to all of the foregoing, all of these facets should be understood to be encompassed by this disclosure.

In the preferred embodiment, the present invention uses PCR technique to amplify a portion of a particular bovine sequence. This sequence may be a portion the Bos taurus testis-specific protein, Y-encoded (TSPY) gene. However, other sequences than bovine sequences might be identified using these primers, and so the invention may not be restricted to just bovine sequences. This invention has uniquely identified two primers that are complementary to this bovine sequence found only in the Y chromosome, the Bos taurus TSPY gene. While other sequences have been used to identify other aspects of the Y chromosome, apparently these primers are uniquely designed to identify this portion of the Y chromosome.

The preferred embodiment of this invention is a specific set of oligonucleotide primers ([SEQ. ID No. 1] and [SEQ. ID No. 2]) for PCR amplification of a specific region of the bovine Y chromosome DNA sequence. Any oligonucleotide probe may be used that is internal to the sequence amplified by the PCR primers ([SEQ. ID No. 1] and [SEQ. ID No. 2]). The label can be any one of the art recognized labels commonly used in DNA blotting.

Two oligonucleotides, [5'-GTGATCCGGCATATAGCTGAGA-3' (SEQ ID No. 1) and 5'-TGGTCGCTGATCAGGATGGAA-3' (SEQ ID No. 2)], have been designed based on the DNA sequence data of the bovine TSPY gene from GenBank. These two oligonucleotides function as specific primers for PCR amplification of the portion of the bovine TSPY gene. The PCR was performed following the protocol as disclosed herein in examples below. The results are described in detail below by the inventor.

Having described the invention in brief, the following examples are given to illustrate specific applications of the invention. These specific examples are not intended to limit the scope of the invention described in this application.

VII. EXAMPLES

The following were the amplification protocol, including the primer sequences, the reagents and the results.

1. PCR Amplification

The reagents used in this invention were listed as follows:

Molecular grade water (Sigma W-3500);

dNTPs (10 mM mix of each deoxyribonucleoside-triphosphates);

Taq DNA Polymerase (5U/µl: Sigma D-1806. 10×reaction buffer is included);

10×reaction buffer (100 mM Tris-HCl, pH 8.3, 500 nM KCl, 15 mM $MgCl_2$);

Forward primer (100 ng/µl) 5'-GTG ATC CGG CAT ATA GCT GAG A-3';

Reverse primer (100 ng/µl) 5'-TGG TCG CTG ATC AGG ATG GAA-3'; and

Bovine Test DNA (10–50 ng/reaction).

Master mix for 50 µl reaction was prepared following the following recipe:

| Reagents | Volume (µl) |
|---|---|
| Water | 38.75 |
| 10X Buffer | 5 |
| dNTPS | 1 |
| Forward primer | 2 |

-continued

| Reagents | Volume (µl) |
|---|---|
| Reverse primer | 2 |
| Taq polymerase | 0.25 |
| Bovine Test DNA | 1 |

The amplification reaction parameters for the amplification cycles were denaturation for 1 min at 94 degree(s) C., annealing of primers for 1 min at 56 degree(s) C., and primer extension for 3 seconds at 72 degree(s) C. The thermocycler parameter settings were as follows:

| Step | Temperature | Time |
|---|---|---|
| 1 | 94° C. | 30 seconds |
| 2 | 94° C. | 30 seconds |
| 3 | 56° C. | 30 seconds |
| 4 | 72° C. | 30 seconds (Repeat steps 2–4 for 30 cycles) |
| 5 | 72° C. | 5 minutes |
| 6 | 4° C. | Soak |

2. Demonstration of Specificity

Both the forward (SEQ ID NO.1) and reverse primers (SEQ ID NO. 2) were evaluated for their ability to amplify a portion of Y chromosome sequence. With a bull or steer DNA a 488 base pair product was amplified. The primers generated the appropriately-sized fragments from DNA preparations from blood samples of bulls when compared to the known standard DNA from bulls. The fact that the primers did not generate a detectable PCR product with DNA from cows suggests that the primers are Y-chromosome sequence specific.

The above example, incorporated as if fully set forth here in text, shows the procedure and results such that one with ordinary skill in the art could duplicate the efforts to produce the specific primers. As shown, the forward primer (SEQ NO. 1) is 5'-GTG ATC CGG CAT ATA GCT GAG A-3' and the reverse primer (SEQ NO. 2) is 5'-TGG TCG CTG ATC AGG ATG GAA-3'. Naturally, these primers may be varied in length or other alterations as long as the functional aspects were retained to hybridize with and to amplify the TSPY gene to indicate gender. This could include from 8–20 nucleotides of the sequences. These primers amplify using the PCR method approximately 488 base pair product of the Y chromosome. Naturally, as those with ordinary skill in the art would understand, the above primer sequences could vary to some degree such that the functional derivative would still be specific for a portion of the Y chromosome. Additionally, while specific reagents and buffers are described and while proportions are disclosed, a variety of buffers and reagents and varying proportions could be used in conjunction with the specific primers of SEQ ID NO.1 and SEQ ID NO.2. Thus, for example any buffering means or any buffering proportions which produce similar or acceptable results in conjunction with SEQ ID NO.1 and SEQ ID NO.2 to identify a specific region of the Y chromosome should be considered included in this invention. Similarly, any reagent means or any reagent proportions which produce similar or acceptable results in conjunction with SEQ ID NO.1 and SEQ ID NO.2 to identify a specific region of the Y chromosome should be considered included in this invention. Other parameters, such as the parameters of the thermocyler or other similar devices, could be varied to accomplish the goals and purposes of the invention.

The present invention is also directed to a kit or reagent system useful for practicing the methods described herein.

Such a kit will contain a reagent combination comprising the essential elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and usually including written instructions for the performance of assays. The kit of the present invention may include any configurations and compositions for performing the various assay formats described herein.

In all cases, the reagent system will comprise a pair of oligonucleotide primers that flank the DNA sequence of interest which is to be amplified and detected, as described herein. Preferably, those primers are (1) SEQ ID NO:1 and (2) SEQ ID NO:2 and they may be detectably labeled. Preferably, the kit will also contain additional reagents useful in carrying out a PCR amplification. A kit according to the present invention can additionally include ancillary chemicals such as the buffers and components of the solution in which binding of the oligonucleotide to the target DNA takes place.

Obviously, many modifications and variations of the present invention are possible in light of the above teachings. It is therefore to be understood that, within the scope of the appended claims, the invention may be practiced otherwise than as specifically described.

The discussion included in this application is intended to serve as a basic description. The reader should be aware that the specific discussion may not explicitly describe all embodiments possible; many alternatives are implicit. The market place and manufacturing concerns may dictate the appropriate embodiments for the present invention. Particularly with respect to the discussion, it should be understood that a number of changes may be made without departing from the essence of the present invention. In this regard, it is intended that such changes—to the extent that they substantially achieve the same results in substantially the same way—will still fall within the scope of the present invention. It also may not fully explain the generic nature of the invention and may not explicitly show how each feature or element can actually be representative of a broader function or of a great variety of alternative or equivalent elements. Again, these are implicitly included in this disclosure. Where the invention is described in sequence-oriented terminology, each element of the sequence implicitly performs a function. Sequence discussions or claims may not only be included for the sequence described, but also method or process claims may be included to address the functions the invention and each element performs. Although the methods related to the system are being included in various detail, only an initial discussion directed toward the sequences have been included. Naturally, that discussion could have some application to the various other methods and aspects discussed throughout the disclosure. Neither the description nor the terminology is intended to limit the scope of the claims which will be included in a full patent application.

It should be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

Each of the various elements of the invention and claims may also be achieved in a variety of manners. This disclosure should be understood to encompass each such variation, be it a functional derivative, such as under high stringency, a method or process embodiment of the sequences, or even merely a variation of any element of these. Particularly, it should be understood that as the disclosure relates to elements of the invention, the words for each element may be expressed by equivalent terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all action may be expressed as a means for taking that action or as an element which causes that action. Similarly, each physical element or compositions disclosed should be understood to encompass a disclosure of the action which that physical element or composition facilitates. Regarding this last aspect, the disclosure of a "buffer" should be understood to encompass disclosure of the act of "buffering" whether explicitly discussed or not—and, conversely, were there only disclosure of the act of "buffering", such a disclosure should be understood to encompass disclosure of a "buffer." Such changes and alternative terms are to be understood to be explicitly included in the description.

In addition, it should be understood that, in the claims and in the application, the term "comprising" is meant to have an inclusive meaning rather than an exclusive one. It should be interpreted in its most expansive form so as to afford the applicant the broadest coverage legally permissible. Therefore, in countries, such as Australia, this term is not intended to have an exclusive, or more limited, meaning.

Any references mentioned in the application for this patent are hereby incorporated by reference, however, to the extent statements might be considered inconsistent with the patenting of this invention such statements are expressly not to be considered as made by the applicant.

What is claimed is:

1. A polymerase chain reaction primer the nucleotide sequence of which consists of 5'-GTGATCCGGCATATAGCTGAGA-3' (SEQ ID NO:1).

2. A polymerase chain reaction primer the nucleotide sequence of which consists of 5'-TGGTCGCTGATCAGGATGGAA-3' (SEQ ID NO:2).

3. A primer pair used for amplifying DNA of the bovine TSPY gene by polymerase chain reaction, wherein the primer pair comprises a first primer comprising the nucleotide sequence of 5'-TGATCCGGCATATAGCTGAGA-3' (SEQ ID No. 1), and a second primer the nucleotide sequence of 5'-TGGTCGCTGATCAGGATGGAA-3' (SEQ ID No. 2).

4. The primer pair used for amplifying DNA of the bovine TSPY gene by polymerase chain reaction according to claim 3, wherein said bovine TSPY gene comprises Bos taurus TSPY gene.

5. A kit useful to detect the presence of a portion of DNA sequence from Y chromosome, comprising:
   a a first container containing a first oligonucleotide primer comprising the nucleotide sequence 5'-GTGATCCGGCATATAGCTGAGA-3' (SEQ ID No. 1), wherein said first oligonucleotide primer binds to a specific Y chromosome polynucleotide sequence; and
   b at least a second container containing a reagent useful in performance of a polyrnerase chain reaction amplification.

6. A kit useful to detect the presence of a portion of DNA sequence from Y chromosome, comprising:
   a a first container containing a second oligonucleotide primer comprising the nucleotide sequence 5'-TGGTCGCTGATCAGGATGGAA-3' (SEQ ID No. 2), wherein said second oligonucleotide primer binds to a specific Y chromosome polynucleotide sequence; and
   b at least a second container containing a reagent useful in performance of a polymerase chain reaction amplification.

7. A kit useful to detect the presence of a portion of DNA sequence from Y chromosome according to claims 5 or 6, wherein said first container contains both said first oligonucleotide primer (SEQ ID No. 1) and said second oligonucleotide primer (SEQ ID No. 2), and wherein said first oligonucleotide primer (SEQ ID No. 1) and said second oligonucleotide primer (SEQ ID No. 2) each bind to a specific Y chromosome polynucleotide sequence.

8. A kit useful to detect the presence of a portion of DNA sequence from Y chromosome according to claim 5, wherein said at least second container contains a DNA polymerase enzyme.

9. A kit useful to detect the presence of a portion of DNA sequence from Y chromosome according to claim 5, further comprising a third container containing a reagent to detect said specific Y chromosome polynucleotide sequence after amplification.

10. A method of detecting a specific Y chromosome sequence by polymerase chain reaction, comprising the steps of:
    a amplifying a specific Y chromosome polynucleotide sequence with a primer pair, wherein said primer pair comprises a first primer comprising the nucleotide sequence of 5'-GTGATCCGGCATATAGCTGAGA-3' (SEQ ID No. 1) and a second primer comprising the nucleotide sequence of 5'-TGGTCGCTGATCAGGATGGAA-3' (SEQ ID No. 2); and
    b detecting the polynucleotide product of said step of amplifying said specific Y chromosome polynucleotide.

11. A method of identifying the gender of an animal, comprising the steps of:
    a obtaining a meat sample from said animal;
    b amplifying a target nucleic acid sequence in said meat with a primer comprising the nucleotide sequence of 5'-GTGATCCGGCATATAGCTGAGA-3' (SEQ ID No. 1);
    c isolating amplified products from said genetic material;
    d determining the existence of Y chromosome polynucleotide sequence in said meat.

12. The method of identifying the gender of an animal according to claim 11, further comprising the step of amplifying said a second target nucleic acid sequence in said meat with a primer comprising the nucleotide sequence of 5'-TGGTCGCTGATCAGGATGGAA-3' (SEQ ID No. 2).

13. The method of identifying the gender of an animal according to claims 11 or 12, further comprising the step of amplifying the said first target nucleotide sequence and said second nucleotide sequence with a primer pair, wherein said primer pair comprises a first primer comprising the sequence of 5'-GTGATCCGGCATATAGCTGAGA-3' (SEQ ID No. 1) and a second primer comprising the sequence of 5'-TGGTCGCTGATCAGGATGGAA-3' (SEQ ID No. 2).

14. A method of amplifying a specific Y chromosome polynucleotide sequence by polymerase chain reaction, comprising the steps of:
    a establishing a specific Y chromosome polynucleotide sequence in a solution;
    b providing a primer pair, wherein said primer pair comprises a first primer comprising the sequence of 5'-GTGATCCGGCATATAGCTGAGA-3' (SEQ ID No. 1) and a second primer comprising the sequence of 5'-TGGTCGCTGATCAGGATGGAA-3' (SEQ ID No. 2) in said solution;

c denaturing said specific Y chromosome sequence;

d annealing each of said primer pair to a specific region on said specific Y chromosome sequence; and e extending each of said primer pair on said specific Y chromosome sequence using said specific Y chromosome sequence as a template to amplify a portion of said Y chromosome sequence.

15. The method of amplifying a specific Y chromosome sequence by polymerase chain reaction according to claim 7, further comprising repeating the steps of denaturing said specific Y chromosome sequence, annealing each of said primer pair to a specific region on said specific Y chromosome sequence, and extending each of said primer pair on said specific Y chromosome sequence using said specific Y chromosome sequence as a template to amplify a portion of said Y chromosome sequence.

16. A method of identifying the gender of an animal by polymerase chain reaction, comprising the steps of:

a establishing a DNA material from a sample of meat of said animal in a solution;

b providing a primer pair, wherein said primer pair comprises a first primer comprising the sequence of 5'-GTGATCCGGCATATAGCTGAGA-3' (SEQ ID No. 1) and a second primer comprising the sequence of 5'-TGGTCGCTGATCAGGATGGAA-3' (SEQ ID No. 2) in said solution;

c denaturing said DNA material to produce two single stranded DNA sequences;

d annealing each of said primer pair to a specific region on each of said single stranded DNA sequences which sequences are complementary to each of said primer sequences;

e extending each of said primer pair on each of said single stranded DNA sequences using each of said single stranded DNA sequences as templates to amplify a specific region of each of said single stranded DNA sequences;

f repeating said steps of denaturing said DNA material to produce two single stranded DNA sequences; annealing each of said primer pair to a specific region on each of said single stranded DNA sequences which sequences are complementary to each of said primer sequences; extending each of said primer pair on each of said single stranded DNA sequences using each of said single stranded DNA sequences as templates to amplify a specific region of each of said single stranded DNA sequences; and g detecting the presence of said specific regions from said DNA material wherein said specific regions have been amplified following said steps of c, d and e and wherein the presence of said specific regions from said DNA material is indicative of male genomic material in said DNA material.

* * * * *